United States Patent [19]

Glossmann

[11] Patent Number: 4,794,187

[45] Date of Patent: Dec. 27, 1988

[54] $^{35}$S-LABELLED 1,4-DIHYDROPYRIDINES

[75] Inventor: Hartmut Glossmann, Heuchelheim, Fed. Rep. of Germany

[73] Assignee: Bayer Aktiengesellschaft, Leverkusen, Fed. Rep. of Germany

[21] Appl. No.: 505

[22] Filed: Jan. 5, 1987

[30] Foreign Application Priority Data

Jan. 11, 1986 [DE] Fed. Rep. of Germany ....... 3600593

[51] Int. Cl.$^4$ .................. C07D 211/90; C07D 413/04; C07D 401/12
[52] U.S. Cl. .................................... 546/321; 546/271; 544/365
[58] Field of Search ................. 546/321, 271; 544/365

[56] References Cited

PUBLICATIONS

Pichat, L. Chem Abstracts 75:9827f.

Primary Examiner—Mary C. Lee
Assistant Examiner—Dale A. Bjorkman
Attorney, Agent, or Firm—Sprung Horn Kramer & Woods

[57] ABSTRACT

A radioactively labelled dihydropyridine compound of the formula

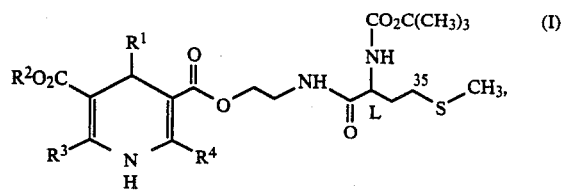

in which
- $R^1$ represents a phenyl radical which is optionally substituted once or twice, identically or differently, by halogen, nitro, trifluoromethyl or difluoromethoxy, or $R^1$ represents benzoxadiazolyl,
- $R^2$ represents a straight-chain or branched alkyl which has up to 8 carbon atoms and which is optionally substituted by cyano, phenyl, halogen, N-benzyl-N-methylamino, N-phenylpiperazino or by alkoxy having up to 4 carbon atoms, and
- $R^3$ and $R^4$ are identical or different and each represents a cyano or represents a straight-chain or branched alkyl which has up to 6 carbon atoms, is optionally interrupted in the chain by one oxygen atom and is optionally substituted by hydroxyl or amino. The compounds are useful in investigating the pharmacokinetics and pharmacodynamics of dihydropyridines, especially for determining metabolism, modes of elimination and organ-specific action.

4 Claims, No Drawings

35S-LABELLED 1,4-DIHYDROPYRIDINES

BACKGROUND OF THE INVENTION

1. Field of the Invention

The invention relates to 1,4-dihydropyridines which are radioactively labelled with $^{35}S$, to a process for their preparation and to their use for the testing of medicaments or other substances using radioreceptor assays and for the determination of the blood plasma levels of dihydropyridines.

2. Background Information

Calcium antagonists are defined as substances which block the passage of calcium through the calcium channels of the cell membrane. They are used therapeutically in the following areas, inter alia: angina pectoris, cardiac arhythmias, high blood pressure and vasospasm [D. J. Triggle, Calcium antagonists—Basic Chemical and Pharmacological Aspects, pages 1–18, in G. B. Weiss "New Perspectives on Calcium Antagonists", American Physiological Society, Bethesda, Maryland USA (1981)].

Calcium antagonists belong to various classes of chemical substances, the representatives of the 1,4-dihydropyridines being among the most effective since they block the passage of calcium through the calcium channels of the cell membrane of the smooth muscles even at low concentrations. This blockade is stereoselective in the case of chiral 1,4-dihydropyridines [A. Fleckenstein (1983), R. A. Janis and D. J. Triggle (1983), R. Towart, E. Wehinger, H. Meyer "Effects of unsymmetrical ester substituted 1,4-dihydropyridine derivatives and their optical isomeres on contraction of smooth muscle, *Naunyn-Schmiedeberg's Arch. Pharmacol.*, 317, 183–5 (1981)].

In this connection, the use of dihydropyridines radioactively labelled with tritium or $^{125}I$ for the characterization of binding sites of these drugs (receptors) has been described [H. Glossmann, D. R. Ferry, F. Lübbecke, R. Mews, F. Hoffmann, "Calcium channels—Direct identification with radioligand binding studies", TIPS, 3, 431–7, (1982); DE-OS (German Published Specification) No. 3,341,806].

Furthermore, 1,4-dihydropyridines labelled with tritium or $^{125}$iodine have been used for the blood plasma level determination of calcium antagonists and for the autoradiographic visualization of their receptors [R. Quirin, "Autoradiographic localization of a calcium channel antagonist-3H-nitrendipine, binding site in rat brain", *Neuroscience Lett.*, 36, 267–71, (1983); DE-OS (German Published Specification) 3,341,806].

However, in view of the regulation on the disposal of radioactive wastes which is in force at present, substances which contain $^{125}I$, and especially $^3H$, are objectionable. Likewise, the radioactively labelled 1,4-dihydropyridines hitherto known frequently have only inadequate affinity and specificity for the corresponding receptors.

Hence, it was necessary to find radioactively labelled 1,4-dihydropyridines which are suitable for the testing of medicaments using radioreceptor assays, have a high specific and radiochemical stability, are straightforward to prepare, have a sufficiently short half-life, can be disposed of without difficulty and which, in particular, have high affinity and specificity for the 1,4-dihydropyridine receptors.

SUMMARY OF THE INVENTION

The present invention now relates to 1,4-dihydropyridines which are radioactively labelled with $^{35}S$ and are of the general formula (I)

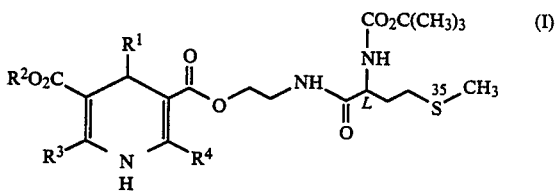

in which
  $R^1$ represents a phenyl radical which is optionally substituted once or twice, identically or differently, by halogen, nitro, trifluoromethyl or difluoromethoxy, or represents benzoxadiazolyl,
  $R^2$ represents straight-chain or branched alkyl which has up to 8 carbon atoms and which is optionally substituted by cyano, phenyl, halogen, N-benzyl-N-methylamino, N-phenylpiperazino or by alkoxy having up to 4 carbon atoms, and
  $R^3$ and $R^4$ are identical or different and each represents cyano or represents straight-chain or branched alkyl which has up to 6 carbon atoms, is optionally interrupted in the chain by one oxygen atom and is optionally substituted by hydroxyl or amino.

Preferred compounds of the general formula (I) are those
in which
  $R^1$ represents 2-nitrophenyl, 3-nitrophenyl, 2,3-dichlorophenyl, 2-chlorophenyl, 2-trifluoromethylphenyl, 2-difluoromethoxyphenyl or benzoxadiazolyl,
  $R^2$ represents straight-chain or branched alkyl which has up to 6 carbon atoms and which is optionally substituted by fluorine, chlorine, bromine, N-benzyl-N-methylamino or by methoxy, and
  $R^3$ and $R^4$ are identical or different and each represents straight-chain or branched alkyl having up to 4 carbon atoms, or represent hydroxymethyl.

Particularly preferred compounds of the general formula (I) are those
in which
  $R^1$ represents 2-nitrophenyl, 3-nitrophenyl, 2,3-dichlorophenyl or 2-trifluoromethylphenyl,
  $R^2$ represents straight-chain or branched alkyl which has up to 6 carbon atoms and is optionally substituted by methoxy, and
  $R^3$ and $R^4$ represent methyl.

Depending on the nature of the substituents, the compounds according to the invention can exist in stereoisomeric forms which are not related as image and mirror image (diastereomers). The invention relates to both the mixtures of diastereomers and the racemic forms.

The compounds according to the invention are prepared by reaction of dihydropyridine derivatives of the general formula (II)

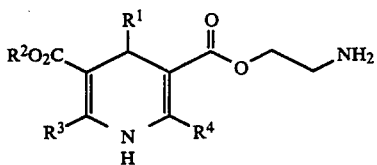

in which

R[1]–R[4] have the abovementioned meaning, with t-butoxycarbonyl-L-$^{35}$S-methionine N-succinimidyl ester of the formula (III)

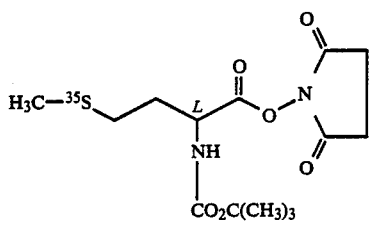

in inert organic solvents.

The reaction can be illustrated by the following equation:

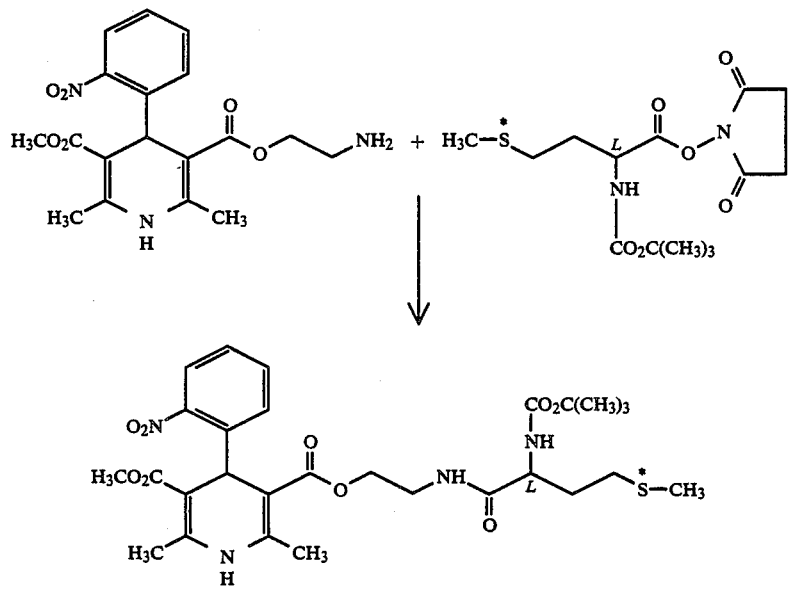

DETAILED DESCRIPTION OF THE INVENTION

Suitable solvents for reaction are the customary inert organic solvents which are not changed under the reaction conditions. These preferably include alcohols such as methanol, ethanol, propanol or isopropanol, or ethers such as diethyl ether, dioxane or tetrahydrofuran, or DMF, hexamethylphosphoric triamide or halogenated hydrocarbons such as, for example, methylene chloride, chloroform or carbon tetrachloride, or acetonitrile or ethyl acetate. It is equally possible to use mixtures of the said solvents.

The reaction is carried out in a temperature range from −30° C. to +80° C., preferably from −20° C. to +40° C.

The reaction can be carried out under atmospheric pressure as well as under elevated or reduced pressure. In general, it is carried out under atmospheric pressure.

It has proved favorable to carry out the reaction in a particular pH range. In general, the reaction is carried out in a pH range from 7 to 11. Where appropriate, for this purpose a base such as triethylamine, or a buffer mixture such as, for example, borate buffer or phosphate buffer, is added.

In carrying out the reaction, in general 1 to 100, preferably 1 to 50, mol of dihydropyridine are used for 1 mol of tert.-butoxycarbonyl-L-$^{35}$S-methionine N-succinimidyl ester.

The dihydropyridines of the general formula (II) which are used as starting materials are known or can be prepared by known methods [U.S. Pat. No. 3,985,758; EP-AS (European Published Specification) 151,006].

The tert.-butoxycarbonyl-L-$^{35}$S-methionine N-succinimidyl ester of the formula (III) which is radioactively labelled with $^{35}$S and is used as starting material is known (can be bought).

The $^{35}$S-labelled 1,4-dihydropyridines according to the invention are particularly well suited for the testing of medicaments by in vitro and in vivo tests, for the autoradiographic visualization of the corresponding dihydropyridine receptors in particular organs, and for the determination of blood plasma levels of dihydropyridines.

The introduction of the radioisotope $^{35}$S has the following advantages: [35]S is a pure $\beta$-emitter with a maximum energy of 0.167 MeV. The half-life is 87.4 days and is thus considerably shorter than that of [3]H. At a specific radioactivity of 1300–1500 Ci/mmol, the compounds according to the invention have a surprisingly high affinity for 1,4-dihydropyridine receptors, for example in the central nervous system (CNS), in vessels, in skeletal muscles and in the coronary region. Thus, the compound of Example 1 has a dissociation rate constant (at 37° C.) of 0.070±0.01 min$^{-1}$ on skeletal muscle, and of 0.02 min$^{-1}$ (37° C.) for the brain receptor. The dissociation constant at 37° C. for the skeletal muscle receptor is 7±3 pmolar which is about 100 times less than that of nimodipine.

Moreover, the compounds which are radioactively labelled with $^{35}S$ have high counting efficiency and allow rapid and extremely high-resolution autoradiographic visualization of the 1.4-dihydropyridine receptors.

The compounds labelled according to the invention are administered by customary methods, for example enterally or parenterally, in particular orally and intravenously.

The compounds according to the invention are preferably used for investigating the pharmacokinetics and the pharmacodynamics of dihydropyridines, in particular for determining metabolism, modes of elimination, and organ-specific actions.

EXAMPLE

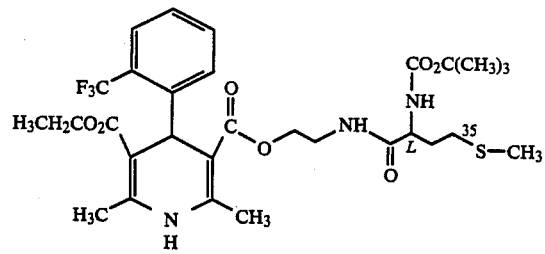

0.5 mCi of tert.-butoxycarbonyl-L-$^{35}$S-methionine N-succinimidyl ester (1450 Ci/mmol corresponding to 0.34 nmol) are mixed with 10 nmol of 3-(2-aminoethyl) 5-ethyl 1.4-dihydro-2.6-dimethyl-4-(2-trifluoromethylphenyl)pyridine-3,5-dicarboxylate in 10 μl of borate buffer pH 8.4 (0.1M) and 10 μl of ethanol in the dark at 0° C. under nitrogen for 2 h. The products are fractionated on silica gel with elution on thin layer chromatography or HPLC, and the desired derivative is obtained in radiochemically pure form and in good yield. The Rf with the eluting agent ethyl acetate-diethyl ether (30:70) is 0.66±0.1.

It will be appreciated that the instant specification and claims are set forth by way of illustration and not limitation, and that various modifications and changes may be made without departing from the spirit and scope of the present invention.

What is claimed is:

1. A radioactively labelled dihydropyridine compound of the formula

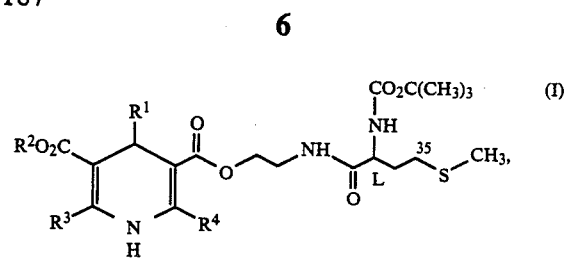

in which
$R^1$ represents a phenyl radical which is unsubstituted or substituted once or twice by an identical or different substituent selected from the group consisting of halogen, nitro, trifluoromethyl and difluoromethoxy, or $R^1$ represents benzoxadiazolyl,
$R^2$ represents a straight-chain or branched alkyl which has up to 8 carbon atoms and which is unsubstituted or substituted by cyano, phenyl, halogen, N-benzyl-N-methylamino, N-phenylpiperazino or by alkoxy having up to 4 carbon atoms, and
$R^3$ and $R^4$ are identical or different and each represents a cyano or represents a straight-chain or branched alkyl which has up to 6 carbon atoms, is not interrupted or is interrupted in the chain by one oxygen atom and is unsubstituted or substituted by hydroxyl or amino.

2. A compound according to claim 1, wherein $R^1$ is selected from the group consisting of 2-nitrophenyl, 3-nitrophenyl, 2,3-dichlorophenyl, 2-chlorophenyl, 2-trifluoromethylphenyl, 2-difluoromethoxyphenyl and benzoxadiazolyl, $R^2$ represents a straight-chain or branched alkyl which has up to 6 carbon atoms and which is unsubstituted or substituted by fluorine, chlorine, bromine, N-benzyl-N-methylamino or methoxy, and $R^3$ and $R^4$ are identical or different and each represent a straight-chain or branched alkyl having up to 4 carbon atoms, or represents hydroxymethyl.

3. A compound according to claim 1, wherein $R^1$ is selected from the group consisting of 2-nitrophenyl, 3-nitrophenyl, 2,3-dichlorophenyl and 2-trifluoromethylphenyl, $R^2$ represents a straight-chain or branched alkyl which has up to 6 carbon atoms and is unsubstituted or substituted by methoxy, and $R^3$ and $R^4$ represent methyl.

4. A compound according to claim 1 of the formula

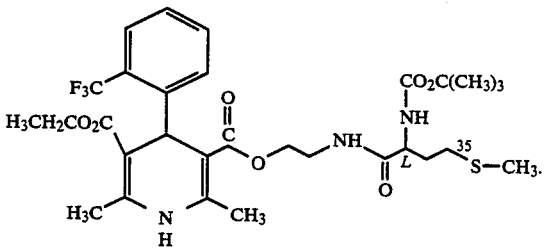

* * * * *